United States Patent
Ecksten

(10) Patent No.: US 10,398,723 B1
(45) Date of Patent: Sep. 3, 2019

(54) HYALURONAN-CONTAINING COMPOSITION AND USE THEREOF FOR MITIGATION AND/OR PREVENTION OF INFLAMMATION AND/OR PAIN

(71) Applicant: Viscos, LLC, Fortville, IN (US)

(72) Inventor: Deborah A. Ecksten, Fortville, IN (US)

(73) Assignee: Viscos, LLC, Fortville, IN (US)

( * ) Notice: Subject to any disclaimer, the term of this patent is extended or adjusted under 35 U.S.C. 154(b) by 202 days.

(21) Appl. No.: 15/051,033

(22) Filed: Feb. 23, 2016

Related U.S. Application Data

(60) Provisional application No. 62/119,803, filed on Feb. 23, 2015.

(51) Int. Cl.
*A61K 31/728* (2006.01)
*A61K 31/10* (2006.01)

(52) U.S. Cl.
CPC ............ *A61K 31/728* (2013.01); *A61K 31/10* (2013.01)

(58) Field of Classification Search
CPC ...... A61K 31/10; A61K 31/19; A61K 31/192; A61K 31/194; A61K 31/728; A61K 47/12; A61K 47/36
See application file for complete search history.

(56) References Cited

U.S. PATENT DOCUMENTS

| | | | | |
|---|---|---|---|---|
| 5,071,878 A | * | 12/1991 | Herschler | A61K 8/46 514/711 |
| 6,607,745 B2 | * | 8/2003 | Leneau | A61K 9/0095 424/400 |
| 8,598,144 B1 | * | 12/2013 | Smith | A61K 9/0053 514/62 |
| 2007/0237816 A1 | * | 10/2007 | Finkelstein | A61K 31/10 424/464 |
| 2011/0171187 A1 | * | 7/2011 | Moore | A61K 45/06 424/93.51 |

FOREIGN PATENT DOCUMENTS

| EP | 1444984 A1 | * | 8/2004 | ............ A61K 31/10 |
|---|---|---|---|---|
| WO | 2007133747 A2 | | 11/2007 | |

OTHER PUBLICATIONS

Adjei, et al., "Pulmonary delivery of peptide drugs: effect of particle size on bioavailability of leuprolide acetate in healthy male volunteers", Pharmaceutical Research 7(6), 565-569 (1990).

Chien, et al., "Enhanced Hyaluronic Acid Production in Bacillus Subtilis by Coexpressing Bacterial Hemoglobin", Biotechynol Prog 23, 1017-1022 (2007).
Chien, et al., "Hyaluronic acid production by recombinant Lactococcus lactis", Appl Microbiol Biotechnol 77, 339-346 (2007).
Chong, et al., "Aerobic cultivation of *Streptococcus zooepidemicus* and the role of NADH oxidase", Biochem Eng J 16, 153-162 (2003).
Chong, et al., "Amplifying the Cellular Reduction Potential of *Streptococcus zooepidemicus*", J Biotechnol 100, 33-41 (2003).
Cowman, et al., "The Content and Size of Hyaluronan in Biological Fluids and Tissues", Frontiers in Immunology 6, 261 (2015).
Kantor, et al., "Association Between Use of Specialty Dietary Supplements and C-Reactive Protein Concentrations", American Journal of Epidemiology 176(11), 1002-1013 (2012).
Kawashima, et al., "Pulmonary delivery of insulin with nebulized DL-lactide/glycolide copolymer (PLGA) nanospheres to prolong hypoglycemic effect", J Controlled Release 62(1-2), 279-287 (1999).
Krahulec, et al., "Increase in hyaluronic acid production by *Streptococcus equi* subsp. *zooepidemicus* strain deficient in β-glucuronidase in laboratory conditions", Appl Microbiol Biotechnol 71, 415-422 (2006).
Liu, et al., "Microbial production of hyaluronic acid: current state, challenges, and perspectives", Microbial Cell Factories 10, 99 (2011).
Liu, et al., "Pulmonary delivery of free and liposomal insulin", Pharm Res 10(2), 228-232 (1993).
Mao, et al., "A recombinant *E. coli* bioprocess for hyaluronan synthesis", Appl Microbiol Biotechnol 84, 63-69 (2009).
Mao, et al., "Recombinant synthesis of hyaluronan by *Agrobacterium* sp", Biotechnol Prog 23, 1038-1042 (2007).
Prasad, et al., "Hyaluronic acid production is enhanced by the additional co-expression of UDP-glucose pyrophosphorylase in Lactococcus lactis", Appl Microbiol Biotechnol 86, 273-283 (2010).
Qian, et al., "Pulmonary delivery of a GLP-1 receptor agonist, BMS-686117", Int J Pharm 366, 218-220 (2009).
Widner, et al., "Hyaluronic Acid Production in Bacillus subtilis", Appl Environ Microbiol 71, 3747-3752 (2005).
Wuthrich, "The proinflammatory role of hyaluronan—CD44 interactions in renal injury", Nephrology Dialysis Transplantation 14(11), 2554-2556 (1999).
Yu, et al., "Metabolic engineering of *Escherichia coli* for biosynthesis of hyaluronic acid", Metabolic Eng 10, 24-32 (2008).
Usha, et al., "Randomised, Double-Blind, Parallel, Placebo-Controlled Study of Oral Glucosamine, Methylsulfonylmethane and their Combination in Osteoarthritis", Clin Drug Invest 24(6), 353-363 (2004).

* cited by examiner

*Primary Examiner* — Leigh C Maier
(74) *Attorney, Agent, or Firm* — Viksnins Harris Padys Malen LLP

(57) ABSTRACT

Disclosed herein is inter alia a composition comprising hyaluronan and methylsulfonylmethane. The composition is useful for the mitigation and/or prevention of inflammation and/or pain.

6 Claims, No Drawings

US 10,398,723 B1

HYALURONAN-CONTAINING COMPOSITION AND USE THEREOF FOR MITIGATION AND/OR PREVENTION OF INFLAMMATION AND/OR PAIN

CROSS-REFERENCE TO RELATED APPLICATIONS

The present application claims priority on the basis of U.S. provisional application Ser. No. 62/119,803, filed Feb. 23, 2015, which is hereby incorporated by reference.

FIELD

A composition and/or method such as is described in various embodiments herein relates to a hyaluronan-containing composition and use thereof for mitigation and/or prevention of inflammation and/or pain.

BACKGROUND

A variety of research confirms that hyaluronan is present throughout the striated and smooth musculature of the cardiovascular, respiratory and reproductive system, as well as throughout the fascia and inside the healthy joint capsules of the human body. Its presence contributes to elasticity throughout these muscle and connective tissue systems, and cushions the articulation of the joints. While hyaluronan is in many respects ubiquitous, its importance to the proper functioning of muscle, fascia, connective tissues (ligaments & tendons), and lining of internal organs is noteworthy. (Mary K. Cowman et al., "The content and size of hyaluronan in biological fluids and tissues," Frontiers in Immunology 2015, Vol. 6, Page 261.)

It has long been a goal of both traditional and allopathic medicine, as well as of nutrition, to mitigate and/or prevent inflammation and pain. This goal has proven elusive, with remedies and supplements showing inadequate effectiveness and/or questionable safety. There has accordingly been a long-felt need for a composition useful for the mitigation and/or prevention of inflammation and/or pain. Contemporary consumers have expressed strong preferences for compositions of natural origin for therapeutic and nutritional purposes. However, the art has been known to teach that natural compositions such as hyaluronan may promote inflammation (Rudolf P. Wuthrich, "The proinflammatory role of hyaluronan-CD44 interactions in renal injury," Nephrology Dialysis Transplantation 1999, Vol. 14, Pages 2554-2556) and that natural compositions such as methylsulfonylmethane may not prevent inflammation (Elizabeth D. Kantor et al., "Association between use of specialty dietary supplements and C-Reactive Protein concentrations," American Journal of Epidemiology 2012, Vol. 176, No. 11, Pages 1002-1013). In light of these teachings of the art, it is surprising that a composition and/or method such as is described in various embodiments herein addresses a long-felt need for a natural composition useful for the mitigation and/or prevention of inflammation and/or pain.

SUMMARY OF EMBODIMENTS

Accordingly, provided herein is a composition comprising hyaluronan and/or methylsulfonylmethane and a pharmaceutically acceptable carrier, diluent, or excipient. Such a composition may be administered to a subject and/or self-administered by a subject for the mitigation and/or prevention of inflammation and/or pain.

DETAILED DESCRIPTION

A composition and method such as are described in various embodiments herein now will be described more fully hereinafter. A composition and method such as are described in various embodiments herein may, however, be embodied in many different forms and should not be construed as limited to the embodiments set forth herein; rather, these embodiments are provided so that this disclosure will be thorough and complete, and will fully convey the scope of a process such as is described in various embodiments herein to those skilled in the art. As used in this specification and the claims, the singular forms "a," "an," and "the" include plural referents unless the context clearly dictates otherwise. When used in this specification and the claims as an adverb rather than a preposition, "about" means "approximately" and comprises the stated value and every value within 10% of that value; in other words, "about 100%" includes 90% and 110% and every value in between.

Hyaluronan (HA) is a non-sulfated glycosaminoglycan. It is a linear polymer consisting of repeating disaccharide units of $\beta$-1, 3-N-acetyl glucosamine and $\beta$-1, 4-glucuronic acid. As it is a polymer, HA varies in size. In vivo HA is understood to exist within the range of 5,000 Daltons to 20,000,000 Daltons (average molecular weight). In human synovial fluid, for example, the average molecular weight of HA is 3 to 4 million Daltons. HA purified from human umbilical cord is 3,140,000 Daltons. In certain aspects, HA has an average molecular weight greater than about 1.0 million Daltons. In certain aspects, HA has an average molecular weight greater than about 2.0 million Daltons. In certain aspects, HA has an average molecular weight less than about 20.0 million Daltons. In certain aspects, HA has an average molecular weight less than about 15.0 million Daltons. In certain aspects, HA has an average molecular weight less than about 10.0 million Daltons. In certain aspects, HA has an average molecular weight less than about 5.0 million Daltons. In certain aspects, HA has an average molecular weight between about 1.0 million Daltons and 5.0 million Daltons. In certain aspects, HA has an average molecular weight between about 2.0 million Daltons and 4.0 million Daltons. In certain aspects, HA has an average molecular weight between about 2.0 million Daltons and 3.0 million Daltons. In certain aspects, HA has an average molecular weight between about 2.5 million Daltons and 4.0 million Daltons. In certain aspects, HA has an average molecular weight between 2.5 million Daltons and 2.8 million Daltons. In certain aspects, HA has an average molecular weight of about 2.5 million Daltons, about 2.6 million Daltons, about 2.7 million Daltons, or about 2.8 million Daltons. In certain aspects, HA has an average molecular weight between about 0.5 million Daltons and about 2.5 million Daltons. In certain aspects, HA has an average molecular weight between about 1.0 million Daltons and about 2.0 million Daltons.

HA is naturally produced by animals, including, but not limited to, rooster, pig, rabbit, and human. It is found in connective, epithelial, and neural tissues. HA is found in, for example, skin, cartilage, and vitreous humour. It is a component of the extracellular matrix, and it is made in the plasma membrane. HA is found in rooster combs, and rooster comb-based extraction processes are known in the art. HA is also naturally produced by microorganisms. It is present in the capsules of certain microbial strains, and, therefore, certain strains of microorganisms have been used to produce HA in large quantities. Methods of making HA in microorganisms are known in the art. See, for example, Liu et al., *Microbial Cell Factories* 10:99 (2011). As taught in Liu et al., (2011), supra, the first commercially fermented HA was produced from *Streptococcus zooepidemicus*. This strain remains the most commonly used strain in industrial production of HA (Chong and Nielsen, *Biochem Eng J* 16:153-162 (2003); Chon and Nielsen, *J Biotechnol* 100: 33-41 (2003); and Krahulec and Krahulcova, *Appl Microbiol Biotechnol* 71:415-422 (2006)). One drawback of using *S. zooepidemicus* is the presence of bacterial endotoxins in the HA-containing microbial fermentate produced during streptococcal fermentation. The application of HA produced by *S. zooepidemicus* has been limited in the biomedical field (Chien and Lee, *Appl Microbiol Biotechnol* 77:339-346 (2007); Widner et al., *Appl Environ Microbiol* 71:3747-3752 (2005)).

Recombinant HA production has emerged as an attractive alternative. Hosts for HA production include both Gram-positive and Gram-negative bacteria, including *Bacillus* sp. (Chien and Lee, *Biotechnol Prog* 23:1017-1022 (2007); Widner et al., 2005, supra), *Lactococcos lactis* (Chien and Lee, 2007, *Appl Microbiol Biotechnol*, supra), *Agrobacterium* sp. (Mao and Chen, *Biotechnol Prog* 23:1038-1042 (2007)), and *Escherichia coli* (Yu and Stephanopoulos, *Metabolic Eng* 10:24-32 (2008)).

An *E. coli* strain (JM109) has been engineered into an efficient HA producer by co-expressing the HA synthase from *Pasteurella multocida* and uridine diphosphate (UDP)-glucose dehydrogenase from *E. coli* K5 strain (Mao et al., *Appl Microbiol Biotechnol* 84:63-69 (2009)). The engineered strain produced 0.5 g/L HA in shaker flask and 2.0-3.8 g/L HA in a fed-batch culture process in a 1-L bioreactor (Mao et al., 2009, supra).

*L. lactis* has been engineered by introducing the HA synthetic machinery from the has operon of *S. zooepidemicus*. It was found that the insertion of uridine diphosphate-glucose pyrophosphorylase (hasC) gene, in addition to the HA synthase (hasA) and UDP-glucose dehydrogenase (has B) genes, significantly increases HA production (Prasad et al., *Appl Microbiol Biotechnol* 86: 273-283 (2010)). The recombinant *L. lactis* NZ9000 strain has been transformed with the plasmid pSJR3 (co-expressing hasA, hasB, and hasC genes) and it gave a maximum of 1.8 g/L HA in a 2.4-L batch bioreactor (Prasad et al., 2010, supra).

The hasA gene from *S. zooepidemicus* has been expressed in *B. subtilis* for the production of HA. It was found that the production of UDP-glucuronic acid is limiting in *B. subtilis* and that overexpressing the hasA gene along with the endogenous tuaD gene is sufficient for high-level production of HA in *B. subtilis* (Widner et al., *Appl Environ Microbiol* 71: 3747-3752 (2005)).

*Agrobacterium* sp. ATCC 31749 has been engineered by co-expressing the HA synthase gene from *P. multocida*, along with a kfiD gene encoding UDP-glucose dehydrogenase from *E. coli* K5 strain (Mao et al., *Biotechnol Prog* 23:1038-1042 (2007)). Coexpression of these two heterologous enzymes enables *Agrobacterium* to produce 0.3 g/L HA in shaker flask cultivation (Mao et al., *Biotechnol Prog* 23:1038-1042 (2007)).

HA can be purchased as a purified product from vendors, such as, Sigma (St. Louis, Mo.), Stanford Chemicals (Irvine, Calif.). Purified HA is available in different grades, including food grade, cosmetic grade, eye drop grade, and injection grade. Purified HA is also available as a cross-linked gel.

HA may accordingly be produced by microorganisms through microbial fermentation. The term "microbial fermentate" or "fermentate" as used herein refers to a product of microbial fermentation. In certain aspects, HA is a product of microbial fermentation and therefore is a microbial fermentate comprising HA. A microbial fermentate comprising HA may be abbreviated as "MF-HA." Microbial fermentates comprising HA may vary with respect to purity levels of HA. In certain embodiments, the purity level of HA in MF-HA of the present disclosure is at least about 70%, at least about 75%, at least about 80%, at least about 85%, or at least about 90%. In certain embodiments, the purity level of HA in MF-HA of the present disclosure is at least about 91%, about 92%, about 93%, about 94%, about 95%, about 96%, about 97%, about 98% or about 99%.

In certain aspects, MF-HA may comprise additional components resulting from microbial fermentation. Such additional components, in certain aspects, may include, but are not limited to, fatty acids (e.g., oleic acid, palmitic acid), lactic acid, microbial enzymes (e.g., staphylokinase, catalase, other secreted enzymes with immune modulating properties including a wide range of proteases), vitamins, yeast extract, components of microbial cell walls, and peptides such as those released from animal waste products.

In certain aspects, MF-HA comprises additional bioactive components resulting from a microbial fermentation other than the HA microbial fermentation (i.e., other than the HA). In certain aspects, MF-HA is combined with at least a portion of another microbial fermentate, such as yeast, *lactobacillus*, and *bacillus* species. In certain aspects, MF-HA is combined with a yeast based fermentate, a *lactobacillus* fermentate, or a *bacillus* fermentate. In certain aspects, MF-HA is combined with a probiotic fermentate, including but not limited to a fermentate from *L. casei Shirota* (LcS), *Lactobacillus rhamnosus* GG (LGG), VSL3#, *L. plantarum* LP-K2, *L. casei* (Lc), *B. lactis*, *S. boulardii* (Sb), *E. coli* Nissle 1917 (ECN), *L. fermentum*, *L acidophilus* (La), *Pediococcus pentosaceus, L. paracasei, E. coli, B. longum, Lactobacillus plantarum* LP BFE 1685, LP MB452, *B. bifidum, Lactobacillus rhamnosus, Lactobacillus acidophilus, B. lactis* 420, *B. lactis* HN019, *Lactobacillus acidophilus* NCFM, *L. salivarius* Ls-33, *S. thermophilus, Bacteroides thetaiotaomicron, Lactobacillus helveticus* R0052, *S. cerevisiae* UFMG 905, *L. gasseri, L. amylovorus, L. gallinarum*, and *L. johnsonii*.

In certain aspects, HA of the present disclosure is formulated into a consumable composition comprising HA and a carrier, diluent, or excipient. In certain aspects, the consumable composition is one suitable for consumption by a mammal. In certain aspects, the consumable composition is one suitable for consumption by a human. In this regard, the present disclosure further provides a consumable composition comprising HA and a carrier, diluent, or excipient. In certain aspects, the consumable composition comprises an MF-HA and a carrier, diluent, or excipient. In certain aspects, the HA is the only active ingredient of the consumable composition. In certain aspects, the HA is part of an MF-HA and the HA is the only active ingredient of the consumable composition. In alternative certain aspects, the HA is part of an MF-HA and the HA is one of the active ingredients of the consumable composition. In certain aspects, the MF-HA comprises one or more other components (in addition to the HA) which function(s) as (an) active ingredient(s) in the consumable composition. In certain aspects, the consumable composition comprises the HA and another component of the MF-HA which results from microbial fermentation are the only active ingredients in the consumable composition.

In some embodiments, the HA is present in the consumable composition at a purity level suitable for administration to a subject. In some embodiments, the HA has a purity level of at least about 90%, about 91%, about 92%, about 93%, about 94%, about 95%, about 96%, about 97%, about 98% or about 99%, and a pharmaceutically acceptable diluent, carrier or excipient. The consumable composition in some aspects comprises the HA at a concentration of at least A, wherein A is about 0.001 mg/ml, about 0.01 mg/ml, 0 about 1 mg/ml, about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml or higher. In some embodiments, the consumable composition comprises the active agent at a concentration of at most B, wherein B is about 30 mg/ml, about 25 mg/ml, about 24 mg/ml, about 23 mg/ml, about 22 mg/ml, about 21 mg/ml, about 20 mg/ml, about 19 mg/ml, about 18 mg/ml, about 17 mg/ml, about 16 mg/ml, about 15 mg/ml, about 14 mg/ml, about 13 mg/ml, about 12 mg/ml, about 11 mg/ml, about 10 mg/ml, about 9 mg/ml, about 8 mg/ml, about 7 mg/ml, about 6 mg/ml, about 5 mg/ml, about 4 mg/ml, about 3 mg/ml, about 2 mg/ml, about 1 mg/ml, or about 0.1 mg/ml. In some embodiments, the compositions may contain an active agent at a concentration range of A to B mg/ml, for example, about 0.001 to about 30.0 mg/ml, about 1.0 mg/ml to about 20 mg/ml, about 1.0 mg/ml to about 15 mg/ml, about 1.0 mg/ml to about 10 mg/ml, about 2.5 mg/ml to about 7.5 mg/ml, or about 4.0 mg/ml to about 6.0 mg/ml.

Depending on the route of administration, the particular active agent(s) intended for use, as well as other factors, the consumable composition may comprise additional ingredients, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

Accordingly, in some embodiments, the consumable composition comprises any one or a combination of the following components: acacia, acesulfame potassium, acetyltributyl citrate, acetyltriethyl citrate, agar, albumin, alcohol, dehydrated alcohol, denatured alcohol, dilute alcohol, aleuritic acid, alginic acid, aliphatic polyesters, alumina, aluminum hydroxide, aluminum stearate, amylopectin, α-amylose, ascorbic acid, ascorbyl palmitate, aspartame, bacteriostatic water for injection, bentonite, bentonite magma, benzalkonium chloride, benzethonium chloride, benzoic acid, benzyl alcohol, benzyl benzoate, bronopol, butylated hydroxyanisole, butylated hydroxytoluene, butylparaben, butylparaben sodium, calcium alginate, calcium ascorbate, calcium carbonate, calcium cyclamate, dibasic anhydrous calcium phosphate, dibasic dehydrate calcium phosphate, tribasic calcium phosphate, calcium propionate, calcium silicate, calcium sorbate, calcium stearate, calcium sulfate, calcium sulfate hemihydrate, canola oil, carbomer, carbon dioxide, carboxymethyl cellulose calcium, carboxymethyl cellulose sodium, β-carotene, carrageenan, castor oil, hydrogenated castor oil, cationic emulsifying wax, cellulose acetate, cellulose acetate phthalate, ethyl cellulose, microcrystalline cellulose, powdered cellulose, silicified microcrystalline cellulose, sodium carboxymethyl cellulose, cetostearyl alcohol, cetrimide, cetyl alcohol, chlorhexidine, chlorobutanol, chlorocresol, cholesterol, chlorhexidine acetate, chlorhexidine gluconate, chlorhexidine hydrochloride, chlorodifluoroethane (HCFC), chlorodifluoromethane, chlorofluorocarbons (CFC)chlorophenoxyethanol, chloroxylenol, corn syrup solids, anhydrous citric acid, citric acid monohydrate, cocoa butter, coloring agents, corn oil, cottonseed oil, cresol, m-cresol, o-cresol, p-cresol, croscarmellose sodium, crospovidone, cyclamic acid, cyclodextrins, dextrates, dextrin, dextrose, dextrose anhydrous, diazolidinyl urea, dibutyl phthalate, dibutyl sebacate, diethanolamine, diethyl phthalate, difluoroethane (HFC), dimethyl-β-cyclodextrin, cyclodextrin-type compounds such as Captisol®, dimethyl ether, dimethyl phthalate, dipotassium edentate, disodium edentate, disodium hydrogen phosphate, docusate calcium, docusate potassium, docusate sodium, dodecyl gallate, dodecyltrimethylammonium bromide, edentate calcium disodium, edtic acid, eglumine, ethyl alcohol, ethylcellulose, ethyl gallate, ethyl laurate, ethyl maltol, ethyl oleate, ethylparaben, ethylparaben potassium, ethylparaben sodium, ethyl vanillin, fructose, fructose liquid, fructose milled, fructose pyrogen-free, powdered fructose, fumaric acid, gelatin, glucose, liquid glucose, glyceride mixtures of saturated vegetable fatty acids, glycerin, glyceryl behenate, glyceryl monooleate, glyceryl monostearate, self-emulsifying glyceryl monostearate, glyceryl palmitostearate, glycine, glycols, glycofurol, guar gum, heptafluoropropane (HFC), hexadecyltrimethylammonium bromide, high fructose syrup, human serum albumin, hydrocarbons (HC), dilute hydrochloric acid, hydrogenated vegetable oil, type II, hydroxyethyl cellulose, 2-hydroxyethyl-β-cyclodextrin, hydroxypropyl cellulose, low-substituted hydroxypropyl cellulose, 2-hydroxypropyl-β-cyclodextrin, hydroxypropyl methylcellulose, hydroxypropyl methylcellulose phthalate, imidurea, indigo carmine, ion exchangers, iron oxides, isopropyl alcohol, isopropyl myristate, isopropyl palmitate, isotonic saline, kaolin, lactic acid, lactitol, lactose, lanolin, lanolin alcohols, anhydrous lanolin, lecithin, magnesium aluminum silicate, magnesium carbonate, normal magnesium carbonate, magnesium carbonate anhydrous, magnesium carbonate hydroxide, magnesium hydroxide, magnesium lauryl sulfate, magnesium oxide, magnesium silicate, magnesium stearate, magnesium trisilicate, magnesium trisilicate anhydrous, malic acid, malt, maltitol, maltitol solution, maltodextrin, maltol, maltose, mannitol, medium chain triglycerides, meglumine, menthol, methylcellulose, methyl methacrylate, methyl oleate, methylparaben, methylparaben potassium, methylparaben sodium, microcrystalline cellulose and carboxymethylcellulose sodium, mineral oil, light mineral oil, mineral oil and lanolin alcohols, oil, olive oil, monoethanolamine, montmorillonite, octyl gallate, oleic acid, palmitic acid, paraffin, peanut oil, petrolatum, petrolatum and lanolin alcohols, pharmaceutical glaze, phenol, liquified phenol, phenoxyethanol, phenoxypropanol, phenylethyl alcohol, phenylmercuric acetate, phenylmercuric borate, phenylmercuric nitrate, polacrilin, polacrilin potassium, poloxamer, polydextrose, polyethylene glycol, polyethylene oxide, polyacrylates, polyethylene-polyoxypropylene-block polymers, polymethacrylates, polyoxyethylene alkyl ethers, polyoxyethylene castor oil derivatives, polyoxyethylene sorbitol fatty acid esters, polyoxyethylene stearates, polyvinyl alcohol, polyvinyl pyrrolidone, potassium alginate, potassium benzoate, potassium bicarbonate, potassium bisulfite, potassium chloride, postassium citrate, potassium citrate anhydrous, potassium hydrogen phosphate, potassium metabisulfite, monobasic potassium phosphate, potassium propionate, potassium sorbate, povidone, propanol, propionic acid, propylene carbonate, propylene glycol, propylene glycol alginate, propyl gallate, propylparaben, propylparaben potassium, propylparaben sodium, protamine sulfate, rapeseed oil, Ringer's solution, saccharin, saccharin ammonium, saccharin calcium, saccharin sodium, safflower oil, saponite, serum proteins, sesame oil, colloidal silica, colloidal silicon dioxide, sodium alginate, sodium ascorbate, sodium benzoate, sodium bicarbonate, sodium bisulfite, sodium chloride, anhydrous sodium citrate, sodium citrate dehydrate, sodium chloride, sodium cyclamate, sodium edentate, sodium dodecyl sulfate, sodium lauryl sulfate, sodium metabisulfite, sodium phosphate, dibasic, sodium phosphate, monobasic, sodium phosphate, tribasic, anhydrous sodium propionate, sodium propionate, sodium sorbate, sodium starch glycolate, sodium stearyl fumarate, sodium sulfite, sorbic acid, sorbitan esters (sorbitan fatty esters), sorbitol, sorbitol solution 70%, soybean oil, spermaceti wax, starch, corn starch, potato starch, pregelatinized starch, sterilizable maize starch, stearic acid, purified stearic acid, stearyl alcohol, sucrose, sugars, compressible sugar, confectioner's sugar, sugar spheres, invert sugar, Sugartab, Sunset Yellow FCF, synthetic paraffin, talc, tartaric acid, tartrazine, tetrafluoroethane (HFC), theobroma oil, thimerosal, titanium dioxide, alpha tocopherol, tocopheryl acetate, alpha tocopheryl acid succinate, beta-tocopherol, delta-tocopherol, gamma-tocopherol, tragacanth, triacetin, tributyl citrate, triethanolamine, triethyl citrate, trimethyl-β-cyclodextrin, trimethyltetradecylammonium bromide, tris buffer, trisodium edentate, vanillin, type I hydrogenated vegetable oil, water, soft water, hard water, carbon dioxide-free water, pyrogen-free water, water for injection, sterile water for inhalation, sterile water for injection, sterile water for irrigation, waxes, anionic emulsifying wax, carnauba wax, cationic emulsifying wax, cetyl ester wax, microcrystalline wax, nonionic emulsifying wax, suppository wax, white wax, yellow wax, white petrolatum, wool fat, xanthan gum, xylitol, zein, zinc propionate, zinc salts, zinc stearate, or any excipient in the *Handbook of Pharmaceutical Excipients*, Third Edition, A. H. Kibbe (Pharmaceutical Press, London, UK, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety, discloses various components used in formulating pharmaceutically acceptable compositions and known techniques for the preparation thereof. Except insofar as any conventional agent is incompatible with the consumable compositions, its use in consumable compositions is contemplated. Supplementary active ingredients also can be incorporated into the compositions.

In certain aspects, the consumable composition comprises HA along with one or more antioxidants or other natural bioactive substances. Suitable antioxidants are known in the art and include but are not limited to methyl sulfonylmethane (MSM), phenols (including flavonoids), betalains, phycocyanins, and other natural antioxidant compounds including pigments. Suitable natural bioactive substances include but are not limited to curcumin, tart cherries, L-carnitine, glutathione, and branched chain amino acids (including leucine, isoleucine, valine), zinc, reservatrol, water-soluble vitamins and minerals, and natural sweeteners. In certain aspects, the consumable composition comprises HA and MSM. In certain aspects, the consumable composition comprises about 1% (w/v) to about 10% (w/v) antioxidant or about 1% (w/v) to about 10% (w/v) other natural bioactive substance. In certain aspects, the consumable composition comprises about 1% (w/v) to about 9% (w/v) antioxidant or other natural bioactive substance, about 1% (w/v) to about 8% (w/v) antioxidant or other natural bioactive substance, about 1% (w/v) to about 7% (w/v) antioxidant or other natural bioactive substance, or about 1% (w/v) to about 6% (w/v) antioxidant or other natural bioactive substance. In certain aspects, the consumable composition comprises about 2% (w/v) to about 10% (w/v) antioxidant or other natural bioactive substance, about 3% (w/v) to about 10% (w/v) antioxidant or other natural bioactive substance, or about 4% (w/v) to about 10% (w/v) antioxidant or other natural bioactive substance. In certain aspects, the consumable composition comprises about 4% (w/v) to about 6% (w/v) antioxidant or other natural bioactive substance.

In certain aspects, the consumable composition comprises HA and citric acid. In certain aspects, the consumable composition comprises about 0.1% (w/v) to about 1.0% (w/v) citric acid. In certain aspects, the consumable composition comprises about 0.1% (w/v) to about 0.9% (w/v) citric acid, about 0.2% (w/v) to about 0.9% (w/v) citric acid, about 0.3% (v/v) to about 0.9% (v/v) citric acid, about 0.4% (v/v) to about 0.9% (v/v) citric acid, about 0.5% (v/v) to about 0.9% (v/v) citric acid, or about 0.6% (v/v) to about 0.9% (v/v) citric acid.

In certain aspects, the consumable composition comprises HA and malic acid. In certain aspects, the consumable composition comprises about 0.1% (w/v) to about 0.5% (w/v) malic acid. In certain aspects, the consumable composition comprises about 0.1% (w/v) to about 0.4% (w/v) malic acid, about 0.1% (w/v) to about 0.3% (w/v) malic acid, or about 0.1% (w/v) to about 0.2% (w/v) malic acid.

In certain aspects, the consumable composition comprises HA and sodium chloride. In certain aspects, the consumable composition comprises about 0.1% (w/v) to about 0.5% (w/v) sodium chloride. In certain aspects, the consumable composition comprises about 0.1% (w/v) to about 0.4% (w/v) sodium chloride, about 0.1% (w/v) to about 0.3% (w/v) sodium chloride, or about 0.1% (w/v) to about 0.2% (w/v) sodium chloride.

In certain aspects, the consumable composition comprises HA and potassium sorbate. In certain aspects, the consumable composition comprises about 0.1% (w/v) to about 0.5% (w/v) potassium sorbate. In certain aspects, the consumable composition comprises about 0.1% (w/v) to about 0.4% (w/v) potassium sorbate, about 0.1% (w/v) to about 0.3% (w/v) potassium sorbate, or about 0.1% (w/v) to about 0.2% (w/v) potassium sorbate.

In certain aspects, the consumable composition comprises HA and a preservative. In certain aspects, the consumable composition comprises about 0.01% (w/v) to about 0.2% (w/v) preservative. In certain aspects, the consumable composition comprises about 0.01% (w/v) to about 0.15% (w/v) preservative. In certain aspects, the preservative is sodium benzoate.

In certain aspects, the consumable composition comprises HA and a xanthan gum. In certain aspects, the consumable composition comprises about 0.1% (w/v) to about 1.0% (w/v) xanthan gum. In certain aspects, the consumable composition comprises about 0.5% (w/v) to about 0.9% (w/v) xanthan gum.

In certain aspects, the consumable composition comprises HA and a sweetener. In certain aspects, the consumable composition comprises about 0.05% (w/v) to about 0.20% (w/v) sweetener. In certain aspects, the consumable composition comprises about 0.08% (w/v) to about 0.15% (w/v) sweetener. In certain aspects, the sweetener is a sugar alcohol, e.g., sucralose.

In certain aspects, the consumable composition comprises HA and a flavoring agent. In certain aspects, the consumable composition comprises about 0.1% (w/v) to about 0.50% (w/v) flavoring agent. In certain aspects, the consumable composition comprises about 0.2% (w/v) to about 0.4% (w/v) flavoring agent.

In certain aspects, the consumable composition is an aqueous solution comprising HA and water. In certain aspects, the consumable composition comprises greater than about 50% (w/v) (e.g., greater than about 75% (w/v), greater than about 80% (w/v), greater than about 85% (w/v), greater than about 90% (w/v).

In certain aspects, the consumable composition comprises HA, water, citric acid, potassium sorbate, sodium benzoate, xanthan gum, flavoring, and sucralose. In certain aspects, the consumable composition comprises HA, water, citric acid, potassium sorbate, sodium benzoate, xanthan gum, flavoring, sucralose, and methylsulfonylmethane. In certain aspects, the consumable composition comprises HA, water, malic acid, citric acid, sodium chloride, potassium sorbate, sodium benzoate, xanthan gum, flavoring, sucralose, and methylsulfonylmethane.

In certain aspects, the HA is present in the consumable composition at a concentration of about 0.1 mg/mL to about 7.0 mg/mL. In certain aspects, the HA is present in the consumable composition at a concentration of about 0.2 mg/mL to about 7.0 mg/mL. In certain aspects, the HA is present in the consumable composition at a concentration of about 0.3 mg/mL to about 7.0 mg/mL. In certain aspects, the HA is present in the consumable composition at a concentration of about 0.4 mg/mL to about 7.0 mg/mL. In certain aspects, the HA is present in the consumable composition at a concentration of about 0.5 mg/mL to about 7.0 mg/mL. In certain aspects, the HA is present in the consumable composition at a concentration of about 0.5 mg/mL to about 1.0 mg/mL. In certain aspects, the HA is present in the consumable composition at a concentration of about 2.5 mg/mL to about 7.0 mg/mL. In certain aspects, the HA is present in the consumable composition at a concentration of about 3.0 mg/mL to about 7.0 mg/mL. In certain aspects, the HA is present in the consumable composition at a concentration of about 4.0 mg/mL to about 7.0 mg/mL. In certain aspects, the HA is present in the consumable composition at a concentration of about 4.0 mg/mL to about 6.0 mg/mL. In certain aspects, the HA is present in the consumable composition at a concentration of about 4.5 mg/mL to about 5.5 mg/mL. In certain aspects, the HA is present in the consumable composition at a concentration of about 4.75 mg/mL to about 5.25 mg/mL. In certain aspects, the HA is present in the consumable composition at a concentration of about 75 mg per 15 ml or about 5 mg/mL. In certain aspects, the HA is about 0.1 to about 1.0% (w/v) of the consumable composition. In certain aspects, the HA is about 0.2 to about 0.8% (w/v) of the consumable composition. In certain aspects, the HA is about 0.4 to about 0.6% (w/v) of the consumable composition.

In certain aspects, the consumable composition comprises natural compounds with anti-inflammatory properties. Such compounds can be derived from botanicals, as well as soil-based, fungus-based, and animal-based products. Examples of animal-based products include milk-based and egg-based products. In certain aspects, the consumable composition comprises resveratrol, anthocyanin, collagen, elastin, proline-rich peptides, and oligo-saccharides.

In certain aspects, the consumable composition comprises additional bioactive components resulting from a microbial fermentation other than the HA microbial fermentation. In certain aspects, the consumable composition comprises at least a portion of another microbial fermentate, such as yeast, *lactobacillus*, and *bacillus* species. In certain aspects, the consumable composition comprises a yeast based fermentate, a *lactobacillus* fermentate, or a *bacillus* fermentate. In certain aspects, the consumable composition comprises a probiotic fermentate, including but not limited to a fermentate from *L. casei* Shirota (LcS), *Lactobacillus rhamnosus* GG (LGG), VSL3#, *L. plantarum* LP-K2, *L. casei* (Lc), *B. lactis*, *S. boulardii* (Sb), *E. coli* Nissle 1917 (ECN), *L. fermentum*, *L acidophilus* (La), *Pediococcus pentosaceus*, *L. paracasei*, *E. coli*, *B. longum*, *Lactobacillus plantarum* LP BFE 1685, LP MB452, *B. bifidum*, *Lactobacillus rhamnosus*, *Lactobacillus acidophilus*, *B. lactis* 420, *B. lactis* HN019, *Lactobacillus acidophilus* NCFM, *L. salivarius* Ls-33, *S. thermophilus*, *Bacteroides thetaiotaomicron*, *Lactobacillus helveticus* R0052, *S. cerevisiae* UFMG 905, *L. gasseri*, *L. amylovorus*, *L. gallinarum*, and *L. johnsonii*. Suitable fermentates are known in the art. In certain aspects, the consumable composition comprises a blend of more than one (e.g., two, three, four, or more) microbial fermentates, such as more than one of the microbial fermentates described herein.

In some embodiments, the foregoing component(s) may be present in the consumable composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the consumable composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the consumable composition at any concentration range, such as, for example from about A to about B. In some embodiments, A is 0.0001% and B is 90%.

The consumable compositions may be formulated to achieve a physiologically compatible pH. In some embodiments, the pH of the consumable composition may be at least 5, at least 5.5, at least 6, at least 6.5, at least 7, at least 7.5, at least 8, at least 8.5, at least 9, at least 9.5, at least 10, or at least 10.5 up to and including pH 11, depending on the formulation and route of administration. In certain embodiments, the consumable compositions may comprise buffering agents to achieve a physiological compatible pH. The buffering agents may include any compounds capable of buffering at the desired pH such as, for example, phosphate buffers (e.g., PBS), triethanolamine, Tris, bicine, TAPS, tricine, HEPES, TES, MOPS, PIPES, cacodylate, MES, and others.

With regard to this disclosure, the HA, or the consumable composition comprising the same, may be administered to the subject via any suitable route of administration. The following discussion on routes of administration is merely provided to illustrate certain embodiments and should not be construed as limiting the scope in any way.

Formulations suitable for oral administration can consist of (a) liquid solutions, such as an effective amount of the active agent of the present disclosure dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the active agent of the present disclosure in a flavor, usually sucrose and acacia or tragacanth, as well as pastilles comprising the active agent of the present disclosure in an inert base, such as gelatin and glycerin, or sucrose and acacia, emulsions, gels, and the like containing, in addition to, such excipients as are known in the art.

In certain aspects, the consumable composition is suitable for oral administration. In certain aspects, the consumable composition is a liquid formulation suitable for oral administration. In certain aspects, the consumable composition is a syrup, a solution (e.g., an aqueous solution), a gum (e.g., a chewing gum), a gel, a paste, a beverage (e.g., a sports drink), a lozenge, a pastille, a tablet, a capsule, a bar (e.g., an energy bar). In certain aspects, the consumable composition is a powder or a seed that may be added to drinks or foods. In certain aspects, the consumable composition suitable for oral administration comprises about 50 mg to about 500 mg HA. In certain aspects, the consumable composition suitable for oral administration comprises about 100 mg to about 300 mg HA. In certain aspects, the consumable composition suitable for oral administration comprises about 150 mg HA. In certain aspects, when the consumable composition is a beverage, the consumable composition comprises about 50 mg to about 500 mg HA. In certain aspects, the beverage comprises about 100 mg to about 300 mg HA. In certain aspects, the beverage comprises about 150 mg HA.

In certain embodiments, the consumable composition may be formulated for pulmonary administration, instead of oral administration. The active agents of the present disclosure, alone or in combination with other suitable components, can be delivered via pulmonary administration and can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa. In some embodiments, the active agent is formulated into a powder blend or into microparticles or nanoparticles. Suitable pulmonary formulations are known in the art. See, e.g., Qian et al., Int J Pharm 366: 218-220 (2009); Adjei and Garren, Pharmaceutical Research, 7(6): 565-569 (1990); Kawashima et al., J Controlled Release 62(1-2): 279-287 (1999); Liu et al., Pharm Res 10(2): 228-232 (1993); International Patent Application Publication Nos. WO 2007/133747 and WO 2007/141411.

In certain embodiments, the consumable composition may be formulated for parenteral administration, instead of oral administration. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The term, "parenteral" means not through the alimentary canal but by some other route such as subcutaneous, intramuscular, intraspinal, or intravenous. The active agent of the present disclosure can be administered with a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-153-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations in some embodiments contain from about 0.5% to about 25% by weight of the active agent of the present disclosure in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations in some aspects are presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions in some aspects are prepared from sterile powders, granules, and tablets of the kind previously described.

Injectable formulations are in accordance with this disclosure. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

In certain embodiments, the consumable composition may be formulated for rectal or vaginal administration, instead of oral administration. For example, the composition can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

In certain embodiments, the consumable composition may be formulated for topical administration, instead of oral administration. In certain aspects, the consumable composition is a cream, ointment, paste, or gel. In certain aspects, the consumable composition is applied topically via a patch.

It will be appreciated by one of skill in the art that, in addition to the above-described consumable compositions, the active agent of the disclosure can be formulated as inclusion complexes, such as cyclodextrin inclusion complexes, or liposomes.

The consumable compositions of the disclosure are useful in methods of decreasing the need for pain medication, as well as other methods, as further described herein, including methods of increasing quality of sleep, methods of increasing energy levels, methods of improving skin softness or firmness, methods of reducing serum levels of IP-10, eotaxin, and/or MCP-1, methods of reducing the occurrence of asthma attacks, methods of treating chronic obstructive pulmonary disease (COPD), methods of reducing menstrual cramping, and methods of reducing diastolic blood pressure. For purposes of the disclosure, the amount or dose of the HA administered should be sufficient to effect, e.g., a therapeutic or prophylactic response, in the subject or animal over a reasonable time frame. For example, the dose of the HA should be sufficient to reduce the need for pain medication in a subject, as described herein in a period of from about 7-14 days or about 1-2 weeks from the time of first administration. In certain embodiments, the time period could be even longer. The dose will be determined by the efficacy of the particular active agent and the condition of the animal (e.g., human), as well as the body weight of the animal (e.g., human) to be treated.

Many assays for determining an administered dose are known in the art. For purposes herein, an assay, which comprises comparing the extent to which asthma is treated upon administration of a given dose of the active agent of the present disclosure to a mammal among a set of mammals, each set of which is given a different dose of the active agent, could be used to determine a starting dose to be administered to a mammal. The extent to which asthma is treated upon administration of a certain dose can be represented by, for example, the differential cell count in bronchioalveolar fluid (BALF), achieved with the active agent in a mouse model of asthma. Methods of measuring BALF are known in the art, including, for instance, the methods described in the EXAMPLES set forth below.

The dose of the active agent of the present disclosure also will be determined by the existence, nature and extent of any adverse side effects that might accompany the administration of a particular active agent of the present disclosure.

In certain aspects, the consumable composition is administered at a dose of about 50 to about 350 mg daily, e.g., about 75 to about 225 mg daily, about 75 to about 150 mg daily, about 150 to about 225 mg daily, about 225 mg daily, or about 300 mg daily. By way of example and not intending to limit the scope of this disclosure, the dose of the consumable composition of the present disclosure for a subject weighing less than 250 lbs. can be about 225 mg HA per day for the first 14 days of consumption, followed by 75-150 mg HA or more daily. For a subject weighing more than 250 lbs. the dose of the consumable composition can be increased, e.g., about 300 mg HA per day for the first 14 days of consumption, followed by 150-225 mg HA or more daily.

The disclosed consumable compositions and formulations may be administered according to any regimen including, for example, daily (1 time per day, 2 times per day, 3 times per day, 4 times per day, 5 times per day, 6 times per day), every two days, every three days, every four days, every five days, every six days, weekly, bi-weekly, every three weeks, monthly, or bi-monthly. Timing, like dosing can be fine-tuned based on dose-response studies, efficacy, and toxicity data.

In certain aspects, the consumable composition is administered daily. By way of example and not intending to limit the scope of this disclosure, the consumable composition of the present disclosure can be administered to a subject weighing less than 250 lbs. in an amount of about 3 tbsp ml per day for the first 14 days of treatment, followed by 1-2 tbsp or more daily. For a subject weighing more than 250 lbs. the consumable composition may be administered in a higher amount, e.g., about 4 tbsp ml per day for the first 14 days of consumption, followed by 2-3 tbsp or more daily.

In some embodiments, the consumable composition described herein is administered to the subject alone, and in alternative embodiments, the consumable composition described herein is administered in combination with another therapeutic agent, e.g., another active agent of different type (e.g., structure). In certain aspects, the consumable composition is administered contemporaneously with the other therapeutic agent. In certain aspects, the consumable composition is administered before the other therapeutic agent. In certain aspects, the consumable composition is administered after the other therapeutic agent. In certain aspects, the therapeutic composition is administered in combination with any one or more of collagen, pomegranate fruit extract, green tea, and the like.

As described herein, the administration of HA to human subjects led to a decrease in serum levels of cytokines IP-10, eotaxin, and MCP-1. Accordingly, provided herein is a method of decreasing levels of IP-10, eotaxin, and/or MCP-1 in a subject in need thereof. The method comprises administering to the subject HA in an amount effective to decrease the level of IP-10, eotaxin, and/or MCP-1 in the subject. In certain aspects, the level is a blood, serum, or plasma level.

IP-10 (also known as CXCL10 chemokine ligand 10, C7, IFI10, INP10, crg-2, mob-1, SCYB10, and gIP-10) is a chemokine of the CXC subfamily and is a ligand of the receptor CXCR3. When IP-10 binds to CXCR3, monocytes are stimulated, adhesion molecule expression is modulated, and migration of natural killer cells and T-cells are stimulated. IP-10 is reported to have interactions with p300, IRF3, p65, and Mac25/AGM. The amino acid sequence of this protein is known and is publically available from the National Center for Biotechnology Information's (NCBI's) Protein database as Accession No. NP_001556.2. The mRNA sequence of this protein is known and is publically available from the NCBI's Nucleotide database as Accession No. NM_001565.

Eotaxin (also known as chemokine ligand 11, SCYA11) is a chemokine of the CC subfamily and is an eosinophil-specific chemokine involved in eosinophilic inflammatory diseases, such as atopic dermatitis, allergic rhinitis, asthma and parasitic infections. Eotaxin is initially produced as a precursor protein comprising a signal peptide. The amino acid sequence of the eotaxin precursor is known and is publically available from the National Center for Biotechnology Information's (NCBI's) Protein database as Accession No. NP_002977. The eotaxin precursor amino acid sequence is provided herein as SEQ ID NO: 3. The signal peptide of the eotaxin precursor is amino acids 1-23, while the mature eotaxin protein sequence is amino acids 24-97. The mRNA sequence of the eotaxin precursor is known and is publically available from the NCBI's Nucleotide database as Accession No. NM_002986.

MCP-1 (also known as chemokine ligand 2, HC11; MCAF; MCP1; SCYA2; GDCF-2; SMC-CF; and HSMCR30) is a chemokine of the CC subfamily. This chemokine is a ligand for the chemokine receptors, CCR2 and CCR4. MCP-1 displays chemotactic activity for monocytes and basophils, but not neutrophils or eosinophils. MCP-1 has been implicated in diseases characterized by monocytic infiltrates, e.g., psoriasis, rheumatoid arthritis and atherosclerosis. Like eotaxin, MCP-1 is initially produced as a precursor protein comprising a signal peptide. The amino acid sequence of the MCP-1 precursor is known and is publically available from the National Center for Biotechnology Information's (NCBI's) Protein database as Accession No. NP_002973. The eotaxin precursor amino acid sequence is provided herein as SEQ ID NO: 5. The signal peptide of the MCP-1 precursor is amino acids 1-23. The mRNA sequence of the eotaxin precursor is known and is publically available from the NCBI's Nucleotide database as Accession No. NM 002982.3. These eotaxin precursor nucleotide sequence of the mRNA is provided herein as SEQ ID NO: 6.

With regard to the method of decreasing levels of IP-10, eotaxin, and/or MCP-1 in a subject in need thereof of the present disclosure, the method comprises administering to the subject HA in an amount effective to decrease the level of IP-10, eotaxin, and/or MCP-1 in the subject. In certain aspects, the level is a blood level, serum level or a plasma level. In certain aspects, the HA is a component of a microbial fermentate and the method comprises administering to the subject a microbial fermentate comprising HA (MFHA). In certain aspects, the MF-HA is a component of a consumable composition and the method comprises administering to the subject a consumable composition comprising MFHA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

Levels of IP-10, eotaxin, and/or MCP-1 may be determined by any suitable means. In certain aspects, the levels are determined by measuring the levels from a biological sample obtained from the subject. In certain aspects, the levels are determined by measuring the levels from serum, blood or plasma obtained from the subject. In certain aspects, the levels are determined by measured using suitable techniques of measuring transcripts known in the art. The measurement of these levels may be a direct measurement of transcripts of IP-10, eotaxin, or MCP-1. Such methods may be considered as involving the measurement of expression levels of transcripts of IP-10, eotaxin, or MCP-1. In certain aspects, the level that is measured is an mRNA transcript level, or a level of the product encoded by the mRNA transcript, e.g., a protein or peptide expression level. Suitable methods of determining expression levels of proteins are known in the art and include immunoassays (e.g., Western blotting, an enzyme-linked immunosorbent assay (ELISA), a radioimmunoassay (MA), immunohistochemical assay, and bead-based immunosorbent detection methods. Suitable methods of determining expression levels of nucleic acids (e.g., mRNA) are known in the art and include quantitative polymerase chain reaction (qPCR), including, but not limited to, real time PCR, Northern blotting and Southern blotting.

Also, provided herein are methods of treating a disease or medical condition in a subject. The method comprises administering to the subject HA in an amount effective to treat the disease or medical condition in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

In certain embodiments, the disease or medical condition is characterized by increased levels of IP-10, eotaxin, and/or MCP-1. In certain embodiments, the disease or medical condition is an inflammatory disease, a cardiovascular disease, or a joint disease. The inflammatory disease, cardiovascular disease, or joint disease may be any one of those described herein. In certain embodiments, the disease or medical condition is any one of the diseases or medical conditions described herein, including, but not limited to, fibromyalgia syndrome, dysmennorhea, adenomyosis, endometriosis, kyphosis, scoliosis, asthma, and osteoarthritis.

In certain aspects, the disease or medical condition characterized by increased levels of IP-10, eotaxin, and/or MCP-1 is an inflammatory disease. As used herein, the term "inflammatory disease" refers to any medical condition or abnormality associated with inflammation. In certain aspects, the inflammatory disease may involve the immune system and may be, for example, an allergic reaction or a myopathy. In certain aspects, the inflammatory disease may be one in which the immune system is not involved, and may be, for example, cancer, atherosclerosis, ischaemic heart disease. In certain aspects, the inflammatory disease is one which affects the airways (e.g., lungs, bronchi, sinuses, and tonsils). In certain aspects, the inflammatory disease is asthma or chronic obstructive pulmonary disease (COPD). In certain aspects, the inflammatory disease is one which affects the joints, muscles, or tendons. In certain aspects, the inflammatory disease is osteoarthritis or rheumatoid arthritis. In certain aspects, the inflammatory disease is acne vulgaris, asthma, an autoimmune disease, an autoinflammatory disease, celiac disease, chronic prostatitis, glomerulonephritis, hypersensitivity, inflammatory bowel disease, pelvic inflammatory disease, reperfusion injury, rheumatoid arthritis, sarcoidosis, transplant rejection, vasculitis, or interstitial cystitis. Accordingly, provided herein are methods of treating any of the inflammatory diseases described herein. The methods of treating the inflammatory disease comprises administering to the subject HA in an amount effective to treat the inflammatory disease. In certain aspects, the subject is administered a consumable composition comprising HA described herein.

Provided herein is a method of treating asthma in a subject. The method comprises administering to the subject HA in an amount effective to treat asthma in the subject. Also, provided herein is a method of reducing the occurrence of asthma attacks in an subject in need thereof. The method comprises administering to the subject HA in an amount effective to reduce the occurrence of asthma attacks in the subject. In certain aspects, the subject is administered a consumable composition comprising HA described herein. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

Provided herein is a method of treating COPD. The method comprises administering to the subject HA in an amount effective to treat COPD in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

In certain aspects, the disease or medical condition characterized by increased levels of IP-10, eotaxin, and/or MCP-1 is a cardiovascular disease. As used herein, the term "cardiovascular disease" refers to any disease affecting the heart or blood vessels. In certain aspects, the cardiovascular disease is selected from coronary heart disease (heart attacks), cerebrovascular disease (stroke), raised blood pressure (hypertension), peripheral arterydisease, rheumatic heart disease, congenital heart disease and heart failure. In certain aspects, the cardiovascular disease is angina, high blood pressure, and varicose veins. Accordingly, provided herein are methods of treating a cardiovascular disease described herein. A method of treating angina in a subject is provided. A method of treating high blood pressure in a subject in need thereof is provided. A method of treating varicose veins is provided. Each of these methods comprise administering to the subject HA in an effective amount. In certain aspects, the subject is administered a consumable composition comprising HA described herein. A method of reducing diastolic blood pressure in a subject in need thereof is provided. The method comprises administering to the subject HA in an amount effective to reduce diastolic blood pressure. In certain aspects, the subject is administered a consumable composition comprising HA described herein. In certain aspects, the HA is a component of a microbial fermentate and the method comprises administering to the subject a microbial fermentate comprising HA (MF-HA). In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

In certain aspects, the disease or medical condition characterized by increased levels of IP-10, eotaxin, and/or MCP-1 is endometriosis. Accordingly, provided herein are methods of treating endometriosis. The method comprises administering to the subject HA in an amount effective to treat endometriosis in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

As shown herein, administration of HA associated with relief of chronic pain and reduced the use of pain medication. Accordingly, methods of reducing pain, e.g., chronic pain, in a subject are provided. In certain embodiments, the method comprises administering to the subject HA in an amount effective to treat the pain. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant. In certain aspects, the pain is chronic back pain. In certain aspects, the pain is exercise-induced pain or menstrual pain (e.g., menstrual cramping).

In certain aspects, the subject suffers from fibromyalgia syndrome (FMS) and the pain is pain associated with FMS. A method of treating fibromyalgia syndrome (FMS) is hence provided. The method comprises administering to the subject HA in an amount effective to treat FMS. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

In certain aspects, the subject suffers from menstrual cramping. A method of treating menstrual cramping in a subject is provided. The method comprises administering to the subject HA in an amount effective to treat the menstrual cramping in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

A method of treating dysmenorrhea or adenomyosis in a subject is provided herein. The method comprises administering to the subject HA in an amount effective to treat the dysmennohea or adenomyosis in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

A method of reducing a subject's need for pain medication is provided herein. The method comprises administering to the subject HA in an amount effective to reduce the subject's need for pain medication. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant. In certain aspects, the pain medication is a non-steroidal anti-inflammatory drug (NSAID), e.g., ibuprofen, naproxen, and the like.

A method of accelerating the time to recovery in a subject is also provided. The method comprises administering to the subject HA in an amount effective to accelerate the time to recovery in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant. In certain aspects, the subject is a subject suffering from a spot injury or exercise-induced pain. In certain aspects, the method accelerates post-surgery recovery or accelerates time to recovery from a trauma or accident, e.g., an auto accident.

A method of supporting healthy joint and muscle function is provided. The method comprises administering to the subject HA in an amount effective to support healthy joint and muscle function. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

A method of treating a joint disease is also provided. The method comprises administering to the subject HA in an amount effective to treat the joint disease in the subject. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects the method comprises administering a consumable composition comprising MF-HA and one or more of: malic acid, citric acid, sodium chloride, potassium sorbate, sodium benzoate, xanthan gum, flavoring, a sucralose, and an antioxidant. In certain aspects, the joint disease is kyphosis or scoliosis.

Administration of HA is also useful for increasing the quality of sleep, increasing energy levels, and increasing skin softness or firmness. Accordingly, a method of increasing the quality of sleep, increasing energy levels, and/or increasing skin softness or firmness is provided herein. The method comprises administering to the subject HA in an amount effective to increase the quality of sleep, increase energy levels, and/or increase skin softness or firmness. In certain aspects, the HA is a component of a microbial fermentate and the method comprises administering to the subject a microbial fermentate comprising HA (MF-HA). In certain aspects, the MF-HA is a component of a consumable composition and the method comprises administering to the subject a consumable composition comprising MF-HA and a pharmaceutically acceptable carrier, excipient, or diluent. In certain aspects, the method comprises administering a consumable composition comprising MF-HA and one or more of: malic acid, citric acid, sodium chloride, potassium sorbate, sodium benzoate, xanthan gum, flavoring, a sucralose, and an antioxidant.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating a disease can provide any amount or any level of treatment. Furthermore, the treatment provided by the method may include treatment of one or more conditions or symptoms or signs of the disease, being treated. Also, the treatment provided by the methods may encompass slowing the progression of the disease. Treatment also encompasses prophylactic treatment, including, e.g., delaying the onset of the disease being treated. In certain aspects, the method delays the onset of the disease by 1 day, 2 days, 4 days, 6 days, 8 days, 10 days, 15 days, 30 days, two months, 4 months, 6 months, 1 year, 2 years, 4 years, or more.

As used herein, the term "decrease" or "reduce" and words stemming therefrom may not be a 100% or complete decrease or reduction. Rather, there are varying degrees of decrease or reduction of which one of ordinary skill in the art recognizes as having a potential benefit or therapeutic effect. In this respect, the compositions may reduce the occurrence of asthma attacks or reduce the need for pain medication to any amount or level. In certain embodiments, the reduction provided by the methods is at least or about a 10% reduction (e.g., at least or about a 20% reduction, at least or about a 30% reduction, at least or about a 40% reduction, at least or about a 50% reduction, at least or about a 60% reduction, at least or about a 70% reduction, at least or about a 80% reduction, at least or about a 90% reduction, at least or about a 95% reduction, at least or about a 98% reduction).

As used herein, the term "increase" and words stemming therefrom may not be a 100% or complete increase. Rather, there are varying degrees of increase of which one of ordinary skill in the art recognizes as having a potential benefit or therapeutic effect. In this respect, the compositions disclosed herein may increase the quality of sleep to any amount or level. In certain embodiments, the increase provided by the methods disclosed herein is at least or about a 10% increase (e.g., at least or about a 20% increase, at least or about a 30% increase, at least or about a 40% increase, at least or about a 50% increase, at least or about a 60% increase, at least or about a 70% increase, at least or about a 80% increase, at least or about a 90% increase, at least or about a 95% increase, at least or about a 98% increase).

In some embodiments, the subject is a mammal, including, but not limited to, mammals of the order Rodentia, such as mice and hamsters, and mammals of the order Logomorpha, such as rabbits, mammals from the order Carnivora, including Felines (cats) and Canines (dogs), mammals from the order Artiodactyla, including Bovines (cows) and Swines (pigs) or of the order Perssodactyla, including Equines (horses). In some aspects, the mammals are of the order Primates, Ceboids, or Simoids (monkeys) or of the order Anthropoids (humans and apes). In some aspects, the mammal is a human.

The following examples are given merely to illustrate the present disclosure and not in any way to limit its scope.

EXAMPLES

Example 1

This example demonstrates inter alia that oral intake of a liquid high molecular weight hyaluronan (HMW HA) associated with relief of chronic pain and reduced use of pain medication.

The following materials and methods were used for a randomized, placebo-controlled, double-blind pilot study.

A randomized, double-blind, placebo-controlled clinical study design was used. Seventy-eight people went through screening and were enrolled into the 4-week study upon signing written informed consent, as approved by Sky Lakes Institutional Review Board (FWA 2603). People were excluded from study participation if they had consumed HA-containing nutritional supplements during the month before the study, were taking prednisone or had done so within 6 months prior to study, had known liver or kidney disease, were taking diuretics medication, undergoing intensive medical treatment for diseases such as cancer or viral illness, and if they were undergoing stressful life events that could affect compliance. People on daily pain medication, non-diuretic blood pressure medication, and cholesterol medication were not excluded from participating in the study. People with fibromyalgia or rheumatoid arthritis and other auto-immune diseases were not excluded solely based on the diagnosis. Screening was performed to ensure normal blood chemistry and heart function as measured by 3-lead ECG. After successful screening, participants were randomized to consume either placebo or a liquid oral HA product. Follow-up visits were scheduled at 2 and 4 weeks.

The liquid hyaluronan-containing consumable product PlayAgain™ and placebo were provided by Viscos, LLC., Fortville, Ind. The active product contained high molecular weight hyaluronan (HA) at a level of 5 mg/mL, and was flavored with sucralose and a mild raspberry flavor. The placebo product had a similar viscosity, sweetness, and flavor, but did not contain HA. The average molecular weight of the HA ranged between 2.5-2.8 million Daltons. Study participants were given a measuring spoon with the test products and instructed to consume 3 tablespoons (45 mL) during the first 2 weeks of the study, and 2 tablespoons (30 mL) during the last 2 weeks of the study.

For this study, each person's anatomical areas of primary and secondary chronic pain, associated with joint stiffness and reduced function, were identified at the screening visit, prior to study start. This information was used at subsequent visits for scoring each person's main complaints, in parallel to overall pain. At each visit, pain levels for both the primary and secondary areas were scored for "pain at rest" and "pain at use", using an unmarked 100 millimeter Visual Analogue Scale (VAS). The VAS were 100 millimeter without increment marks, where one end was labeled "no pain", and the other end was labeled "intense pain". The score was measured on the scale in millimeters and scored in percentage.

At screening, 2-week, and 4-week follow-up, blood was drawn in order to perform a complete blood count (CBC) with differential count, a comprehensive metabolic panel (CMP) and Hepatic Function. At screening and 4-week follow up, a 3-lead electrocardiogram (ECG) was performed.

At each study visit, the study participants went through an interview to monitor adherence to study protocol. Returned product was weighed to track compliance as it pertains to consumption of the allocated test product (Table 1).

TABLE 1

Compliance Based on Weight of Consumed Product

|  | Average compliance |
|---|---|
| Compliance during Phase 1 (3 tbsp/day) | 84.09 |
| Compliance during Phase 2 (2 tbsp/day) | 86.56 |
| Compliance during entire study | 85.79 |

These %s include all 72 study participants.

The number of subjects was based on power calculations based on data from a preliminary open-label pilot study, this study was 90% powered to detect a 10% change. Statistical significance of changes from baseline to later assessments was evaluated by 'between-groups' analysis using the 2-tailed independent t-test. 'Within-subject' analysis was performed using the 2-tailed paired t-test. Statistical significance was indicated if $p<0.05$.

The following results of the randomized, placebo-controlled, double-blind pilot study were observed.

The primary purpose of this 4-week study was to gather data from a placebo-controlled study regarding chronic pain reduction during consumption of oral HMW HA. Sub-group analysis included evaluation of pain medication, pain scores at study start, use of antidepressants, and diagnosis of fibromyalgia. Analysis of pain scores for each person's identified primary area of pain from the 63 study participants who were not diagnosed with FMS (32 in the placebo arm, 31 in the active product arm) showed changes within 2 weeks. A reduction in pain scores was seen for both the placebo group and the group consuming oral HMW HA, however the reduction was more robust in the group consuming oral HMW HA, reaching a statistical trend both when scoring for 'pain when inactive' ($p<0.1$) and when scoring for 'pain when physically active' ($p<0.065$). Analyzing the data for the oral HMW HA group using 'within-subject' analysis, the pain scores when physically active showed a statistically significant reduction at the 2-week visit ($p<0.001$), followed by a mild increase in pain during the last 2 weeks of the study.

Among the 9 study participants with a physician-confirmed diagnosis of FMS (5 in the placebo arm, 4 in the active product arm), the data suggested a statistical trend at the 4 week follow-up, where reduced pain scores reached borderline significance when compared to baseline using 'within-subject' analysis ($p<0.065$). This suggested a slower response in people with a physician-confirmed diagnosis of fibromyalgia syndrome (FMS).

The scores for how much people relied on pain medication during the day showed a mild decrease in the placebo group, and a more robust decrease in the group consuming oral HMW HA, however the difference did not reach statistical significance. Analyzing the reduction within each group using 'within-subject' analysis, showed no significant changes in the placebo group, but the decrease was statistically significant ($p<0.05$) in the use of pain medication during the first 2 weeks in the group consuming oral HMW HA, followed by an increase during the last 2 weeks of the study where people had more physical energy. This should also be interpreted in light of the lower dose consumed during the last 2 weeks (2 tablespoons) as compared to three tablespoons during the first 2 weeks of the study.

When subjects were asked to score their quality of sleep and their physical energy level, a significant increase in self-reported quality of sleep and physical energy levels were seen in the population consuming oral HA, when comparing to the placebo group ($p<0.03$). The improved quality of sleep and physical energy was most distinct during the last 2 weeks of the study, when pain scores had started to increase again, suggesting continued improvement in personal wellness. The improved sleep quality was seen within 2 weeks when compared to baseline for the group consuming oral HMW HA ($p<0.09$), and this improvement reached a high level of significance at 4 weeks ($p<0.01$), data not shown. Self-reported energy levels improved during the last 2 weeks of the study, but did not reach statistical significance ($p<0.07$). When subjects were asked to rate their skin health, statistically significant improvements for skin softness and skin firmness were seen in the group consuming oral HA, but not in the placebo group.

The safety evaluation during the 4 week study included complete blood count with differential count, comprehensive metabolic panel, and 3-lead electrocardiogram (ECG).

The purpose of the CBC analysis was to examine whether consumption of oral HA would result in changes in blood cell numbers, for example if allergies were increased as a reaction to ingredients in the product, or cell production/death in other ways affected. The CBC data did not show any major changes. All group averages remained within the normal ranges for each parameter. An increase in eosinophil numbers was seen for the placebo group, suggesting that some people experienced allergies during the study. No similar increase was seen for the group consuming oral HA; in contrast, a mild decrease in eosinophil numbers was seen in the group consuming oral HMW HA.

The purpose of the comprehensive metabolic panel was to examine whether consumption of oral HMW HA would result in changes in blood chemistry, for example if the consumption of oral HMW HA would lead to stress on liver or kidney function. The CMP data did not show any major changes and all group averages remained within the normal ranges for each parameter. However, using within-subject analysis, there were statistically significant changes seen for several data sets for the group consuming oral HMW HA. The blood levels of sodium, $CO_2$, blood urea nitrogen, creatinine, and albumin were decreased. These effects were very minute, but using the within-subject analysis (paired 2-tailed t-test) reached significance ($p<0.05$).

The glomerular filtration rate (GFR) was in normal range (above 60 mL/minute/1.73 $m^2$) for all study participants at screening and at both subsequent blood draws.

The electrocardiograms (ECG) for all study participants were normal at study start (screening visits), as well as at study exits. Thus, no changes to heart function, as measured by 3-lead ECG, were seen as a result of consumption of oral HMW HA (data not shown).

A discussion of the results follows:

The goal for the study presented here was to evaluate a chronic pain management strategy using oral liquid high molecular weight hyaluronic acid, as an alternative to injected HA. The data has shown that the oral HMW HA is both efficacious and safe. The daily consumption of oral HMW HA resulted in reduced pain and use of main medication already after two weeks. At that time, in the chosen study design, the daily dose was reduced from 3 tablespoons (45 mL) to a maintenance dose of 2 tablespoons (30 mL). During the last 2 weeks of the study, where the maintenance dose was consumed, no further decrease in chronic pain was seen. The self-reported quality of sleep and energy levels continued to increase through the 4-week study, suggesting that the lack of continued reduction in pain scores was due to a combination of the reduced dose of product and increased activity levels. This is typical of chronic pain studies where an initial pain relief is associated with increased physical activity, resulting in either no further change or even a slight increase in pain scores, due to the increased activity.

The non-invasive use of oral high molecular weight HA is an attractive intervention and the effectiveness may stem not only from accumulation of HA in connective tissue. The direct immune modulating properties of HA are multi-facetted, and may happen via CD44- and/or ICAM-1 signaling pathways. With respect to CD44/HA interaction, high and low molecular weight forms of HA have different effects on CD44 clustering, signaling, and downstream cellular behavior such as adhesion. The molecular weight of HA has direct impact on whether pro- or anti-inflammatory effects are prominent, including cross-talk between HA-mediated signaling and the COX-2/prostaglandin pathways. Thus current research has accumulated a convincing volume of documentation of high molecular weight HA's direct anti-inflammatory properties.

The overall safety data included complete blood counts with differential counts, comprehensive metabolic panel of blood markers, and ECG, and showed no significant changes between the two groups. Within the group consuming oral HMW HA, several metabolic markers showed significant changes during the 4 weeks of oral HA consumption. These changes were very small but did reach statistical significance using 'within-subject' analysis, and will need further evaluation. Several of these parameters may possibly relate to a better hydration status. Water/fluid consumption was not tracked during this study; it is possible that consumption of oral HMW HA may have led to a higher intake of fluids. Alternatively, the oral HMW HA may have contributed to a reduced level of inflammation, leading to improved function of organs including the kidneys.

In light of the recent changes in recommended osteoarthritis management, where injectable HA is no longer recommended, alternative methods for managing chronic joint pain are in high demand. The data presented here suggests that high molecular weight HA offers a non-invasive method for pain management in situations involving moderate chronic joint pain affecting mobility. Future work is warranted on the oral BMW HA, and should include detailed assessment of inflammatory status, and encompass different study populations, including fibromyalgia patients with longer study duration, younger study population, athletes, and people recovering from acute trauma. It will also be of interest to evaluate the effects of oral BMW HA on its potential effects on inflammatory problems unrelated to joints and mobility.

Example 2

This example demonstrates inter alia the changes in cytokine levels upon consumption of oral HMW HA.

During the 4-week randomized double-blind placebo-controlled clinical study on chronic pain (described in EXAMPLE 1), blood samples were collected from each participating subject at baseline, at 2 weeks, and at 4 weeks of consumption of either placebo or oral HMW HA. The blood samples were stored at −80 degrees Celsius.

Blood samples were subsequently thawed and the cytokine levels of these samples were assayed using a Luminex XMAP array, which is capable of assaying 27 cytokines of pro-inflammatory, anti-inflammatory, and immune-regulating nature. When comparing the group averages of cytokine levels between the people consuming placebo versus oral MF-HA, a normalization of specific pro-inflammatory cytokines was seen in the group consuming oral HMW HA. The effect was selective and did not uniformly affect all pro- or anti-inflammatory cytokines. Significantly lower serum levels of IP-10, Eotaxin, and MCP-1 were seen in the group consuming oral HMW HA, relative to the placebo group Reduced levels were also observed for Interferon-γ and IL-1b, although the reduction did not meet the level for statistical significance. In contrast, no changes were seen for other pro-inflammatory cytokines.

Example 3

This example demonstrates inter alia an association between consumption of oral HMW HA and increased relief of pain in patients with fibromyalgia syndrome.

Nine patients with confirmed fibromyalgia syndrome (FMS) were evaluated for 4 weeks, as described in Example 1. Of the nine patients, four were placed in the placebo group, and five were placed in the oral BMW HA group. As described in Example 1, data on pain scores were collected from all patients. In those patients who consumed oral HMW HA, a statistical trend for relief of pain in the defined area of each person's primary pain complaint was observed ($p<0.1$). In the patients that consumed oral BMW HA, a 23% decrease in primary pain when the person was physically active was observed after 4 weeks of treatment. In contrast, a 24% increase in the use of pain medication was observed in the placebo group over the same time period.

Subjects (24) diagnosed with FMS are enrolled for a larger clinical study. The subjects are randomized into two groups: a treatment group and a placebo group. Subjects in the treatment group are given oral MF-HA at 2 tablespoons for 4 to 12 weeks. Data on pain scores are collected from all subjects in the study.

Example 4

This example demonstrates inter alia an association between consumption of oral HMW HA and reduced occurrence of asthma attacks.

A patient with a medical history of asthma began consuming oral MF-HA for 12 weeks at a dose of 2 tablespoons daily. Prior to treatment with oral MF-HA, the patient would experience uncontrollable coughing and muscle spasms during asthma attacks. The patient reported a lack asthma attacks in the time period during which s/he consumed oral MF-HA. The lack of asthma attack by this subject while consuming oral HMW HA is consistent with the study described in Example 2, which suggests the association between consumption of oral HMW HA and the regulation of cytokines involved in asthma, including IP-10, MCP-1, and Eotaxin.

To determine the protective effects and the underlying mechanisms of oral BMW HA in asthmatic subjects, a study using a mouse model of allergic asthma ovalbumin (OVA)-induced allergic inflammation is carried out. A total of 50 mice are randomly assigned to five experimental groups: (1) control, (2) model, (3) dexamethasone (2 mg/kg), (4) HMW HA (10 mg/kg) and (5) BMW HA (20 mg/kg). Differential cell count in bronchioalveolar fluid (BALF) is measured by Wright-Giemsa staining. Histological assessment is measured by hematoxylin and eosin (HE) staining. BALF levels of cytokines, including eotaxin, are measured using a Luminex cytokine array.

It is expected that mice in the group treated with BMW HA will inhibit OVA-induced increases in eosinophil count. It is also anticipated that substantially reduced eotaxin levels in BALF compared with the control group, will be observed, suggesting a direct association between reduced eotaxin levels and eosinophil recruitment.

Example 5

This example demonstrates inter alia an association between consumption of oral HMW HA and chronic obstructive pulmonary disease (COPD).

A subject with a medical history of COPD began consuming oral MF-HA. The patient reported a robust relief of COPD symptoms during treatment with oral MF-HA, and a return of COPD symptoms once the treatment with MF-HA ceased. The relief of COPD symptoms experienced by this subject while consuming oral HMW HA is consistent with the study described in Example 2, which suggests the association between consumption of oral HMW HA and the regulation of cytokines involved in COPD, including IP-10, MCP-1, and Eotaxin.

Subjects (12) diagnosed with COPD are enrolled for a 4-month clinical study. The subjects are randomized into two groups: a treatment group and a placebo group. For the first two months of the study, subjects are monitored for symptoms of COPD and their symptoms are recorded. The last two months of the study is the treatment period during which subjects in the treatment group consume MF-HA at a dose of 2 tablespoons/day, and subject in the placebo group consume a similar volume of a liquid matched for taste and viscosity, but not containing MF-HA. Symptoms of COPD are recorded during the treatment period.

It is expected that those subjects consuming MF-HA exhibit COPD symptoms of a moderate magnitude, whereas only a mild and transient reduction in COPD symptoms are exhibited by those in the placebo group.

Example 6

This example demonstrates inter alia an association between consumption of oral HMW HA and reduced menstrual pain.

A study is carried out involving three pre-menopausal women with heavy dysmenorrhea. The women experience excessive bleeding and very painful cramps during menses. During the study, these women are to consume 2-3 tablespoons of HMW HA for several months. It is expected that the women consuming HMW HA will report reduced cramping during menses, which would suggest an association between consumption of MF-HA and reduction in menstrual cramping. The reduction in menstrual cramping by these subjects while consuming oral HMW HA would be consistent with the study described in Example 2, which would suggest the association between consumption of oral HMW HA and the regulation of cytokines involved in dysmenorrhea, including MCP-1.

To further our understanding of the effects of HMW HA on menstrual cramping, a clinical study is performed involving 12 pre-menopausal women with varying degrees of fibromyomas, heavy bleeding during menses, and excessive menstrual pain. The women consume HMW HA daily for 6 months, and their menstrual symptoms, bleeding severity, and use of pain medication during menses is monitored. A significant reduction in bleeding severity, menstrual pain, and use of pain medication during menses is expected to be observed in those women consuming HMW HA.

Example 7

This example demonstrates inter alia a method of testing the effect of oral HMW HA on cardiovascular health.

A three-month clinical study in which 24 adult men and women with moderate hypertension consume MF-HA daily is carried out. Blood pressure is assessed on a monthly basis using a strict protocol for rest prior to measurement, and multiple measurements for each visit.

A significant reduction in diastolic blood pressure when comparing pre- and post-evaluations is expected to be observed upon consumption of HMW HA.

Example 8

This example demonstrates inter alia a method of testing the effect of oral HMW HA on vascular reactivity.

Post-Occlusive Reactive Hyperemia (PORH) is an objective method to study the health, elasticity, and reactivity of peripheral vascular endothelium. A clinical study is performed on 10 males 50-65 years of age. Subjects consume MF-HA for 8 weeks, and the PORH response is evaluated every 4 weeks. Evaluation of vascular health is performed using PeriFlux laser Doppler probes and PORH, wherein the probes are applied distal to a blood pressure cuff (probes on lower forearm, cuff on upper arm; non-dominant arms used). The cuff is inflated to 20% above systolic blood pressure for 3 minutes, and is then released; laser Doppler probes recorded the pre-occlusion, occlusion, and post-occlusion peripheral microvascular blood flow. It is expected that, after 8 weeks of treatment with oral HMW HA, a notable improvement in the response time and magnitude is observed in at least 70% of subjects.

Example 9

This example demonstrates inter alia an association between consumption of oral HMW HA and rapid improvement of muscle and joint function and strength in athletes.

A feasibility study involved 6 actively training endurance athletes who were suffering from chronic pain associated with previous trauma. All 6 athletes reported an increase in muscle strength, performance, and accelerated recovery during the time they consumed oral HMW HA. Time to improvement ranged from 3 days to 14 days, and also involved reducing or eliminating over-the-counter pain medication.

Example 10

This example demonstrates inter alia a method of testing the effects of recovery time after exercise-induced inflammation.

A double-blind, randomized, placebo-controlled, crossover study is performed in 12 healthy but sedentary males, age 25-40 years. The subjects are evaluated twice, with a 1-week wash-out period between assessments. Prior to each assessment, subjects consume either 5 tablespoons of MF-HA, or a placebo. During each assessment, a baseline questionnaire and blood draw is performed. Subjects then perform a 20-minute exercise on a stationary bicycle, with a pre-defined personalized exercise intensity. Blood draws are taken immediately after exercise and again 1 hour after exercise. Subjects are allowed to consume water ad libitum prior to and during the exercise. Blood levels of cytokines are evaluated using Luminex cytokine arrays.

Example 11

This example demonstrates inter alia a method of making a formulation comprising HMW HA composition and a natural antioxidant and testing the effects of this formulation on chronic pain.

An MF-HA-containing formula, blended with MSM is made by combining an MF-HA with MSM, malic acid, citric acid, sodium chloride, potassium sorbate, sodium benzoate, xanthan gum, sucralose, flavor and water. This formulation is marketed under the name of PlayAgainNow™.

An open-label study is carried out to examine the rapid effects on chronic pain conditions associated with oral intake of PlayAgainNow™. Twelve people between the ages of 19-71 years are enrolled upon written informed consent, as approved by a registered Institutional Review Board, and the subject complete the initial study. During the initial 2 weeks of the placebo-controlled study, 3 tablespoons (45 mL) Play AgainNow™ or placebo are consumed daily. Reduction in chronic pain is seen after 2 weeks of consumption of 3 tablespoons of PlayAgainNow™. It is expected that the pain reduction observed during the initial two weeks of the study is associated with significant reduction in the use of pain medication.

Example 12

This example demonstrates inter alia the differences between sources of HMW HA.

Bacteria, such as *Streptococcus zooepidemicus* and *Streptococcus equi*, produce hyaluronic acid. During the production of hyaluronic acid, nutritional substrates used in the culture media may comprise vitamins, yeast extract, and agricultural waste products (plant-, animal-, and fish-based), and microbial metabolites are produced as a fermentation by-product. Some of these products remain in the resulting microbial fermentate. During the production of HA, bacterial metabolites are produced, and are present in the resulting fermentate containing HA, unless steps are taken to remove these metabolites from the fermentate. It is hypothesized that these metabolites contribute to the pool of bioactive compounds in the microbial fermentate containing HA. Additional microbial fermentates are blended in accordance with the above descriptions in some aspects.

The ability of microbial fermentate hyaluronic acid (MF-HA) to inhibit an inflammatory cascade in response to free radical insult is tested in a cell culture model using human polymorphonuclear (PMN) cells in vitro. Briefly, freshly purified human peripheral blood PMN cells are exposed in vitro to either crude MF-HA comprising bacterial metabolites or pure HA (lacking bacterial metabolites). An inflammatory reaction involving a reactive oxygen burst is induced in the PMN cells after exposure to the crude MF-HA or the pure HA. Using an indicator dye that turns fluorescent when exposed to reactive oxygen species (ROS), and performing flow cytometric assessment of the cell cultures, pure HA is found to enhance the inflammatory reaction, whereas the MF-HA reduced the level of ROS produced by the PMN cells. This indicates that the biological activity of MF-HA has significant and unique contribution from the non-HA portion.

The ability of MF-HA to inhibit an inflammatory cascade in response to an inflammatory insult is also tested in a cell culture model using human whole blood cultures from healthy adult donors. Untreated cultures are to serve as a negative control. Cultures treated with lipopolysaccharide (LPS) are to serve as positive controls for inflammation. Whole blood cultures are pre-treated with MF-HA across a wide dose range prior to inducing inflammation by addition of LPS. Culture supernatants are harvested and used to evaluate cytokine production, including the cytokines IL-2, IL-6, IL-8, TNF-a, IP-10, Eotaxin, and MCP-1. Pre-treatment of cultures with MF-HA are expected to show a specific inhibition of inflammatory cytokines. In contrast, pure HA is expected to not inhibit production of inflammatory cytokines.

When comparing the biological activities of pure MF-HA (1% non-HA compounds) and crude MF-HA, it is expected that the pure HA will have a predominantly pro-inflammatory biological activity, in contrast to crude MF-HA where several cytokines are expected to demonstrate anti-inflammatory activity.

Example 13

Surprisingly, in light of the foregoing results and the art, a formulation with favorable properties was developed in which the mass ratio of MSM to HA was about 10:1. In particular, when MSM was included in an aqueous formulation at about 5% wt/vol and HA was included in the formulation at about 0.5% wt/vol, unexpectedly favorable properties were observed. In an aspect, in 15 mL of such a formulation were 750 mg MSM and 75 mg HA. In 15 mL of such a formulation were also Filtered Water, citric acid, malic acid, sodium chloride, potassium sorbate, sodium benzoate, xanthan gum, sucralose and N&A Flavors. To make such a formulation, HA was added stepwise and slowly to water or to an aqueous solution containing some or all other ingredients with slow stirring, for example over the course of 12 or more hours, so as not to create needless bubbles or shearing. A formulation containing 5% wt/vol MSM, 0.5% wt/vol HA, with Filtered Water as the predominant other ingredient, but also optionally containing citric acid, malic acid, sodium chloride, potassium sorbate, sodium benzoate, xanthan gum, sucralose and N&A Flavors, was thereby made. The art has not recognized that efficacy in eliciting various physiological effects is a function of MSM:HA mass ratio, and therefore the MSM:HA mass ratio parameter optimized has not been recognized in the art to be a result-effective variable.

Example 14

Administration of a formulation according to Example 13 was found to decrease inflammatory cell activation in a dose-dependent manner in samples from human subjects. A dose of 0.006 mg/mL, 0.05 g/mL or 0.4 mg/mL (concentration of formulation in culture medium) was employed, but any dose less than 0.006 mg/mL or greater than 0.4 mg/mL or between 0.006 mg/mL and 0.4 mg/mL (concentration of formulation in any diluent) is likewise within the scope of this disclosure. Such a decrease of inflammatory cell activation was different from, and of greater magnitude than, a decrease of inflammatory cell activation elicited by HA or MSM alone. Activation of inflammatory cells was measured, and is verified by assays known in the art, by expression of CD69, a protein expressed on activated white blood cells including T lymphocytes, NK cells, monocytes and PMN cells. Activation of inflammatory cells was measured, and is verified by assays known in the art, by expression of CD25, the alpha chain of the low affinity interleukin-2 (IL-2)

receptor. A statistically significant increase is a function of sample size and variability. An increase such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%. A statistically significant decrease is a function of sample size and variability. A decrease such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%. Treatment of whole blood culture with a formulation according to Example 13 increased activation of Natural Killer (NK) cells and monocytes and decreased activation of T lymphocytes and polymorphonuclear (PMN) cells. Treatment of a peripheral blood mononuclear cell (PBMC) culture with a formulation according to Example 13 decreased activation of NK cells, Natural Killer T (NKT) cells, T lymphocytes and monocytes. In a pre-inflammation culture model, treatment of whole blood culture with a formulation according to Example 13 decreased activation of NK, NKT and T lymphocytes and increased activation of monocytes and PMN cells. In a pre-inflammation culture model, treatment of a PBMC culture with a formulation according to Example 13 increased activation of monocytes. In a post-inflammation culture model, treatment of whole blood culture with a formulation according to Example 13 decreased activation of NK, NKT, T lymphocytes and monocytes. In a post-inflammation culture model, treatment of whole blood culture with a formulation according to Example 13 increased activation of monocytes. Accordingly, treatment with a formulation according to Example 13 is evidenced as decreasing response to lipopolysaccharide (LPS) through a TLR4 receptor, thereby reducing inflammation.

Example 15

Administration of a formulation according to Example 13 was found to decrease release of pro-inflammatory cytokines in a dose-dependent manner in samples from human subjects. A dose of 0.006 mg/mL, 0.05 g/mL or 0.4 mg/mL (concentration of formulation in culture medium) was employed, but any dose less than 0.006 mg/mL or greater than 0.4 mg/mL or between 0.006 mg/mL and 0.4 mg/mL (concentration of formulation in any diluent) is likewise within the scope of this disclosure. Such a decrease was observed consistently in post-inflammation PBMC cultures. A statistically significant decrease is a function of sample size and variability. A decrease such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%. A decrease in release of each of IFN-γ, IL-4, IL-5, IL-6, IL-7, IL-12p70, IL-13, Eotaxin, IP-10, RANTES, IL-10, IL-1rα, PDGF-BB, VEGF and G-CSF was observed upon administration of a formulation according to Example 13. Release of each of IFN-γ, IL-4, IL-5, IL-6, IL-7, IL-12p70, IL-13, Eotaxin, IP-10, RANTES, IL-10, IL-1rα, PDGF-BB, VEGF and G-CSF was measured, and is verified, by one or more assays known in the art.

Example 16

Administration of a formulation according to Example 13 was found to decrease pain in a dose-dependent manner in human subjects. Twelve subjects consumed about 3 tablespoons per day (45 mL per day) of a formulation according to Example 13 for the initial two weeks of a study period, and about 2 tablespoons per day (30 mL per day) of a formulation according to Example 13 for the subsequent two weeks of the study period. Consumption of a formulation according to Example 13 resulted in a significant decrease in pain throughout the study period. A statistically significant decrease is a function of sample size and variability. A decrease such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%. After the first two weeks of the study period, subjects experienced a statistically significant decrease in pain. The decrease in pain was associated with an increase in function of subjects and an increase in interaction by subjects with friends and family members. A statistically significant increase is a function of sample size and variability. An increase such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%.

Example 17

Administration of a formulation according to Example 13 was found to decrease indicia of discomfort and/or inflammation and to increase indicia of activities of daily living in a dose-dependent manner in human subjects. Twelve subjects consumed about 3 tablespoons per day (45 mL per day) of a formulation according to Example 13 for the initial two weeks of a study period, and about 2 tablespoons per day (30 mL per day) of a formulation according to Example 13 for the subsequent two weeks of the study period. Consumption of a formulation according to Example 13 resulted in decreased indicia of discomfort and/or inflammation and increased indicia of activities of daily living. A statistically significant decrease is a function of sample size and variability. A decrease such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%. A statistically significant increase is a function of sample size and variability. An increase such as that observed in this Example may be, by way of example and not of limitation, of at least about 1%, or of at least about 2%, or of at least about 5%, or of at least about 10%, or of at least about 20%, or of at least about 30%, or of at least about 40%, or of at least about 50%, or of at least about 60%, or of at least about 70%, or of at least about 80%, or of at least about 90%. Subjects experienced increased indicia of satisfaction with and/or quality of life. Subjects engaged in increased physical activity. Subjects engaged in increased voluntary social activities. Subjects experienced a decreased dependence on others to assist them with activities of daily living. Subjects experienced decreased indicia of discomfort and/or inflammation.

All references, including publications, patent applications, and patents, cited herein are hereby incorporated by reference to the same extent as if each reference were individually and specifically indicated to be incorporated by reference and were set forth in its entirety herein. Where there is any real or apparent conflict between a reference and this disclosure, this disclosure is of greater authority and accordingly is controlling.

All references, including publications, patent applications, and patents, cited herein are hereby incorporated by reference to the same extent as if each reference were individually and specifically indicated to be incorporated by reference and were set forth in its entirety herein. Where there is any real or apparent conflict between a reference and this disclosure, this disclosure is of greater authority and accordingly is controlling.

The use of the terms "a" and "an" and "the" and similar referents in the context of describing what is disclosed herein (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of what is disclosed herein.

Preferred embodiments are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Many modifications and other embodiments of a composition and method such as are described in various embodiments herein will come to mind to one skilled in the art to which this disclosed process pertains having the benefit of the teachings presented in the foregoing description. Therefore, it is to be understood that a composition and method such as are described in various embodiments herein is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for decreasing pain in a subject comprising orally administering daily to the subject for about four weeks about 45 mL of an aqueous composition consisting of MSM, hyaluronan (HA) prepared by microbial fermentate having an average molecular weight of about 1.0 million to 3.0 million Daltons, citric acid, malic acid, sodium chloride, potassium sorbate, sodium benzoate, xanthan gum, sucralose and one or more flavorants, wherein the composition comprises about 5% wt/vol MSM and about 0.5% HA prepared by microbial fermentate, and wherein the mass ratio of MSM to HA is about 10:1.

2. A method according to claim 1, wherein the subject is a mammal.

3. A method according to claim 1, wherein the subject is a human.

4. The method of claim 1, wherein the method comprises increasing activation of Natural Killer (NK) cells or monocytes.

5. The method of claim 1, wherein the method decreases release of one or more pro-inflammatory cytokines in the subject.

6. A method according to claim 5, wherein the one or more pro-inflammatory cytokines comprise IFN-γ, IL-4, IL-5, IL-6, IL-7, IL-12p70, IL-13, Eotaxin, IP-10, RANTES, IL-10, IL-1rα, PDGF-BB, VEGF or G-CSF.

* * * * *